United States Patent
Clark et al.

(10) Patent No.: US 11,540,814 B2
(45) Date of Patent: Jan. 3, 2023

(54) SYSTEMS, METHODS, AND APPARATUSES FOR ACTIVE THERMAL MANAGEMENT OF ULTRASOUND TRANSDUCERS

(71) Applicant: KONINKLIJKE PHILIPS N.V., Eindhoven (NL)

(72) Inventors: Dennis Dean Clark, Reedsville, PA (US); Jeffrey Scott Hart, Reedsville, PA (US); Ryan Manning, Reedsville, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 649 days.

(21) Appl. No.: 15/564,951

(22) PCT Filed: Apr. 9, 2016

(86) PCT No.: PCT/IB2016/052027
§ 371 (c)(1),
(2) Date: Oct. 6, 2017

(87) PCT Pub. No.: WO2016/162855
PCT Pub. Date: Oct. 13, 2016

(65) Prior Publication Data
US 2018/0125461 A1    May 10, 2018

Related U.S. Application Data

(60) Provisional application No. 62/145,532, filed on Apr. 10, 2015.

(51) Int. Cl.
*A61B 8/00* (2006.01)
*B06B 1/02* (2006.01)
*G10K 11/00* (2006.01)

(52) U.S. Cl.
CPC ............ *A61B 8/546* (2013.01); *A61B 8/4444* (2013.01); *A61B 8/4455* (2013.01); *B06B 1/02* (2013.01); *G10K 11/004* (2013.01); *B06B 1/0292* (2013.01)

(58) Field of Classification Search
None
See application file for complete search history.

(56) References Cited

U.S. PATENT DOCUMENTS 4,272,968 A * 6/1981 Harvill ................. B67D 1/0864
165/133
5,213,103 A    5/1993 Martin et al.
(Continued)

FOREIGN PATENT DOCUMENTS

CN    102728536 A    10/2012
JP    2008086362 A    4/2008
(Continued)

*Primary Examiner* — Amelie R Davis
*Assistant Examiner* — Marjan Saboktakin

(57) ABSTRACT

An ultrasound probe including an active thermal management system is disclosed. The active thermal management system may include a fluid chamber coupled to a transducer assembly of the ultrasound probe. The fluid chamber may include a coolant that may dissipate heat from the transducer assembly. The active thermal management system may further include a heat sink coupled to the fluid chamber and thermal management system. The heat sink may include fins that extend into the coolant. The coolant may be a liquid or a gas. The coolant may be circulated within the fluid chamber by a circulation device. The circulation device may be a pump, a fan, or an impeller. An ultrasound probe may further include a window that forms an enclosure over the lens of the transducer assembly. The enclosure may be fluidly coupled to the fluid chamber and filled with coolant to dissipate heat from the lens.

16 Claims, 7 Drawing Sheets

(56) References Cited

U.S. PATENT DOCUMENTS

| | | | |
|---|---|---|---|
| 5,560,362 A | 10/1996 | Sliwa et al. | |
| 8,475,375 B2 | 7/2013 | Smith et al. | |
| 2007/0232923 A1 | 10/2007 | Asuri | |
| 2008/0146924 A1* | 6/2008 | Smith | G01S 7/52079 600/437 |
| 2009/0030325 A1 | 1/2009 | Hyuga | |
| 2010/0125198 A1 | 5/2010 | Thapliyal et al. | |
| 2011/0077558 A1 | 3/2011 | Ostrovsky et al. | |
| 2015/0265961 A1 | 9/2015 | Davey et al. | |
| 2016/0262288 A1* | 9/2016 | Chainer | H05K 7/20809 |

FOREIGN PATENT DOCUMENTS

| | | | | |
|---|---|---|---|---|
| JP | 2008284003 A | 11/2008 | | |
| JP | 2016202190 A | 12/2016 | | |
| WO | 2014193013 A1 | 12/2014 | | |
| WO | WO-2014193013 A1 * | 12/2014 | | A61N 7/02 |
| WO | WO-2015029637 A1 * | 3/2015 | | A61B 8/4444 |

* cited by examiner

SYSTEMS, METHODS, AND APPARATUSES FOR ACTIVE THERMAL MANAGEMENT OF ULTRASOUND TRANSDUCERS

This application is the U.S. National Phase application under 35 U.S.C. § 371 of International Application No. PCT/IB 2016/052027, filed on Apr. 9, 2016, which claims the benefit of Provisional Application Ser. No. 62/145,532, filed Apr. 10, 2015. These applications are hereby incorporated by reference herein.

BACKGROUND

Ultrasound transducer arrays produce ultrasound waves for a variety of applications such as imaging, cleaning, and therapeutic treatment of tissue. Many ultrasound transducers convert electrical energy into ultrasound waves, and heat may be produced as a byproduct of the conversion. The heat may require dissipation to avoid damaging the transducer and/or a surface with which the ultrasound transducer is in contact. For example, a medical ultrasound transducer may burn the skin of a patient if heat produced by the transducer is not dissipated adequately.

Ultrasound transducers may have active and/or passive thermal management systems. Passive systems may include materials that draw heat away from the transducer. For example, an ultrasound probe may include a backing material below the transducer that may dissipate heat away from the transducer surface. However, current passive thermal management systems may not be adequate for new, higher power ultrasound applications such as shear wave imaging.

Active thermal management systems may include, for example, circulating liquid coolants pumped via conduits adjacent to the transducer array. Coolants may be provided to the conduits via a reservoir within the ultrasound probe or external to the ultrasound probe. Active thermal management systems may be capable of rapidly dissipating heat, active systems may decrease ultrasound probe reliability. For example, a liquid coolant based thermal management system may require circulation tubing and a circulation pump. However, with some liquid coolant based systems, the tubing and pump may be prone to leakage over time as the elements are flexed during use of the ultrasound probe. Leakage of the liquid coolant may damage the internal components of the ultrasound probe and/or reduce the effectiveness of the active thermal management system.

SUMMARY

An example ultrasound probe according to an embodiment of the disclosure may include a transducer assembly including a transducer and a fluid chamber coupled to the transducer assembly and may be configured to dissipate heat from the transducer assembly, the fluid chamber may include an outer shell having an upper surface and a lower surface, wherein the upper surface may be proximate to the transducer assembly and the lower surface may be distal to the transducer assembly, and a hollow interior may be configured to contain a fluid coolant.

An example active thermal management system for an ultrasound probe according to an embodiment of the disclosure may include a fluid chamber that may be configured to couple to a transducer assembly of the ultrasound probe and may be further configured to dissipate heat from the transducer assembly, the fluid chamber may include an outer shell having an upper surface and a lower surface, wherein the upper surface may be proximate to the transducer assembly and the lower surface may be distal to the transducer assembly, a hollow interior that may be configured to contain a fluid coolant, a circulation device that may be configured to circulate the fluid coolant, and a sealed port through the outer shell, wherein the sealed port may be configured to allow electrical coupling of a power source to the circulation device.

A second example ultrasound probe according to an embodiment of the disclosure may include a transducer assembly that may include a lens having a top surface and a bottom surface and a transducer stack coupled to the bottom surface of the lens. The ultrasound probe may also include a fluid chamber that may at least partially enclose the transducer assembly, the fluid chamber may include an outer shell having an upper rim and a lower surface, wherein the upper rim may be proximate to the transducer assembly and the lower surface may be distal to the transducer assembly, a hollow interior that may be configured to contain a fluid coolant, the fluid coolant may be configured to dissipate heat from the transducer assembly, a circulation device that may be configured to circulate the fluid coolant, and a sealed port through the outer shell, wherein the sealed port may be configured to allow electrical coupling of a power source to the circulation device. The ultrasound probe may further include a window coupled to the upper rim of the fluid chamber, the window may be configured to be above and offset from the lens to form an enclosure between the window and the top surface of the lens in fluid communication with the fluid chamber, wherein the fluid coolant may fill the enclosure.

DETAILED DESCRIPTION

Figure 1:
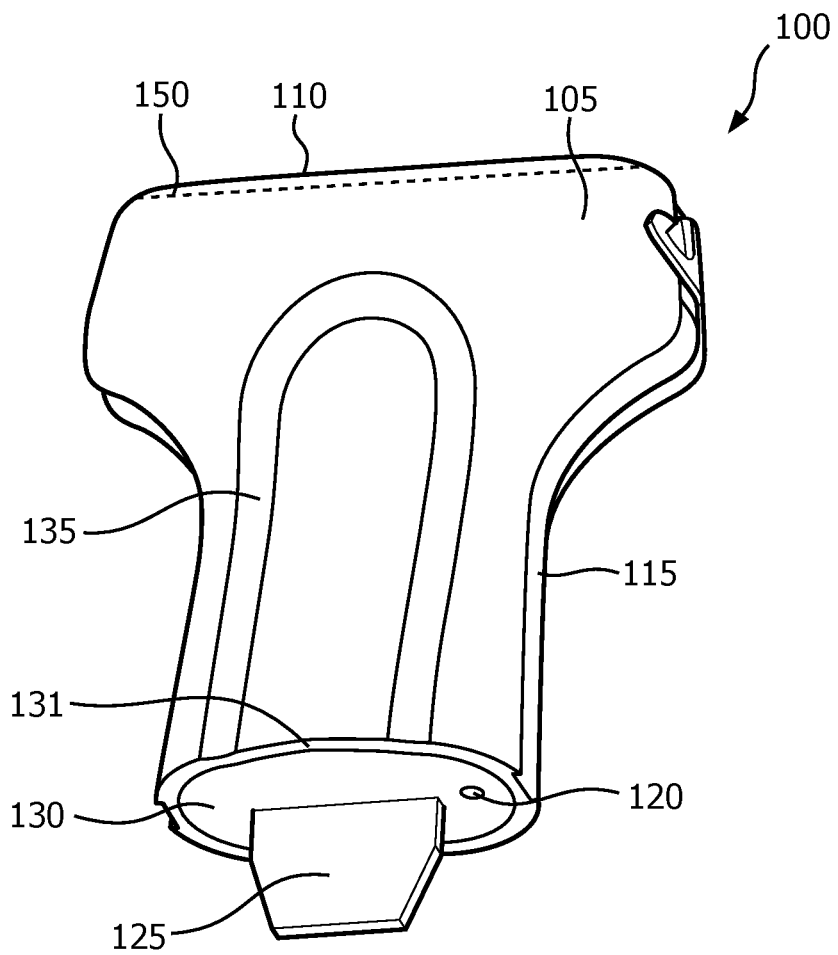
FIG. 1 is a schematic illustration of a fluid chamber according to an embodiment of the disclosure.

The following description of certain exemplary embodiments is merely exemplary in nature and is in no way intended to limit the invention or its applications or uses. In the following detailed description of embodiments of the present systems and methods, reference is made to the accompanying drawings which form a part hereof, and in which are shown by way of illustration specific embodiments in which the described systems and methods may be practiced. These embodiments are described in sufficient detail to enable those skilled in the art to practice the presently disclosed systems and methods, and it is to be understood that other embodiments may be utilized and that structural and logical changes may be made without departing from the spirit and scope of the present system.

The following detailed description is therefore not to be taken in a limiting sense, and the scope of the present system is defined only by the appended claims. The leading digit(s) of the reference numbers in the figures herein typically correspond to the figure number, with the exception that identical components which appear in multiple figures are identified by the same reference numbers. Moreover, for the purpose of clarity, detailed descriptions of certain features will not be discussed when they would be apparent to those with skill in the art so as not to obscure the description of the present system.

An ultrasound probe may be used for imaging, medical therapy, or other applications. The ultrasound probe includes an ultrasound transducer to produce and receive ultrasound signals (e.g., waves, pulses, sequences). The transducer may be included in a transducer assembly. The transducer may generate heat as it produces and/or receives ultrasound signals. If the temperature of the transducer increases above a threshold temperature, the transducer may be damaged and/or a patient may be injured. For example, supporting electronic components of the transducer assembly may melt and become inoperable or a patient being imaged may suffer a burn on the skin.

To manage the increase in temperature of the transducer, the probe may include an active thermal management system to dissipate the heat generated by the transducer. The active thermal management system may include a fluid chamber filled with a fluid coolant. A circulation device may be included within the fluid chamber to circulate and/or agitate the coolant throughout the fluid chamber. The fluid chamber may be coupled to the transducer assembly and/or a heat sink coupled to the transducer assembly. Coupling the fluid chamber to the transducer assembly and/or heat sink may allow heat dissipation without the use of tubing and/or other conduits. This may reduce or eliminate potential leakage of coolant in the probe.

Coupling the fluid chamber to the transducer assembly and/or heat sink without the use of tubing and/or other conduits may facilitate assembly of an ultrasound probe. For example, the fluid chamber may be a separate modular unit that may be installed in an ultrasound probe during assembly. In some embodiments, the modular unit may include the fluid chamber and a heat sink. In some embodiments, the modular unit may be configured to be press fit into another ultrasound probe component, for example, a probe frame, a transducer assembly, and/or a probe housing. In some embodiments, the modular unit may be configured to be snap fit into a resilient ultrasound probe component. This may reduce or eliminate fasteners used to install the modular unit. In some embodiments, the modular unit may facilitate retrofitting of existing ultrasound probes with an active thermal management system.

The fluid chamber may be embedded in and/or partially enclosed by an ultrasound probe frame. The probe frame may be used to provide support for a transducer assembly, printed circuit boards, and/or other probe components. In some embodiments, the fluid chamber may replace the probe frame.

The coolant in the fluid chamber may dissipate heat from the transducer assembly and/or heat sink and distribute the heat throughout the coolant and fluid chamber. The heat may be dissipated from the fluid chamber to a probe housing and/or to the air surrounding the probe. The coolant and fluid chamber may dissipate the heat over a wide area. This may prevent the occurrence of "hot spots," that is, localized sections of the ultrasound probe that have a greater temperature than the surrounding probe. Hot spots may damage other portions of the ultrasound probe and/or make the ultrasound probe uncomfortable or dangerous to handle by a user.

FIG. 1 is a schematic illustration of a fluid chamber 100 according to an embodiment of the disclosure. The fluid chamber 100 may be used in an active thermal management system in an ultrasound probe. The fluid chamber 100 may include an outer shell 105 with a hollow interior (not shown). The hollow interior may be filled with a coolant 150. The outer shell 105 may comprise molded plastic, metal, and/or another material impermeable to the coolant 150. The outer shell 105 may be formed as a single integral unit or as multiple components coupled together to form the outer shell 105. For example, the outer shell 105 may include two injection-molded halves coupled together by epoxy or other coupling method that is impermeable to the coolant. The outer shell 105 may be contoured to fit within the interior of a hand-held ultrasound probe. For example, as shown in FIG. 1, the outer shell 105 may have a three dimensional "T" shape, where the wide portion of the "T" may be proximate a transducer assembly and/or heat sink. In other examples, the outer shell 105 may be a cylinder, a rectangular prism, or an ovoid. Other shapes of the outer shell 105 may also be used.

The outer shell 105 may include grooves 115 to accommodate electrical components of the ultrasound probe. For example, the grooves 115 may accommodate printed circuit boards (PCBs) and/or flexible circuits of the ultrasound probe (neither shown). The outer shell 105 may include additional grooves 135 that may promote intimate connection with an interior surface of a probe housing (not shown). For example, the probe housing may include grooves to promote a non-slip grip for a sonographer. The additional grooves 135 may be configured to receive the grooves of the probe housing's inner surface. In another example, the probe housing may include grooves on the inner surface that mate with the additional grooves 135 to facilitate alignment of the outer shell 105 and the probe housing during probe assembly. In some embodiments, the additional grooves 135 may be omitted.

The outer shell 105 may include a bottom surface 130. The bottom surface 130 may be flat as illustrated in FIG. 1. In some embodiments, the bottom surface 130 may be contoured to accommodate the shape of the interior of the ultrasound probe. The bottom surface may include a tang 125. The tang 125 may extend perpendicularly from the bottom surface 130. The tang 125 may be located in the center of the bottom surface 130 as illustrated in FIG. 1. In some embodiments, the tang 125 may extend from an edge of the bottom surface 130, for example, edge 131. In some embodiments, multiple tangs may be present. The tang 125 may be trapezoidal, square, half-circle, or another shape. The shape of the tang 125 may be chosen based at least in part, on the shape of the interior of the ultrasound probe. The tang 125 may facilitate mechanical coupling between the fluid chamber 100 and a bend relief ferrule (not shown) of the ultrasound probe. The tang 125 may further facilitate thermal coupling between a cable assembly (not shown) of the probe and the fluid chamber 100.

The bottom surface 130 may include a sealed port 120. The sealed port 120 may be impermeable to fluid and/or only permit fluid flow in a single direction. The sealed port 120 may facilitate electrical coupling between a power source and a circulation device (neither shown) located in the interior of the fluid chamber 100. The sealed port 120 may facilitate filling of the fluid chamber 100 with a coolant. In some embodiments, the sealed port may be used to incorporate a fluid expansion chamber and/or bladder to compensate a change in fluid volume, for example, due to temperature change. In some embodiments, the bottom surface 130 may include multiple sealed ports. Separate sealed ports may be used for electrical coupling and filling of the fluid chamber 100. In some embodiments, the sealed port 120 may be located on another surface of the outer shell 105. For example, the sealed port 120 may be located in the groove 115. The sealed port 120 may be implemented with rubber, silicone, and/or other suitable fluid-impermeable material.

The outer shell 105 may include an upper surface 110. The upper surface 110 may be sized to match the dimensions of a heat sink and/or a portion of a transducer assembly (neither shown). In some embodiments, the upper surface 110 is a closed surface of the outer shell 105. In some embodiments, the upper surface 110 may include an upper rim defining a periphery of an opening of the fluid chamber 100. When the upper surface 110 is open, the coolant of the fluid chamber 100 may come into direct contact with a portion of the heat sink and/or a portion of the transducer assembly.

Figure 2:
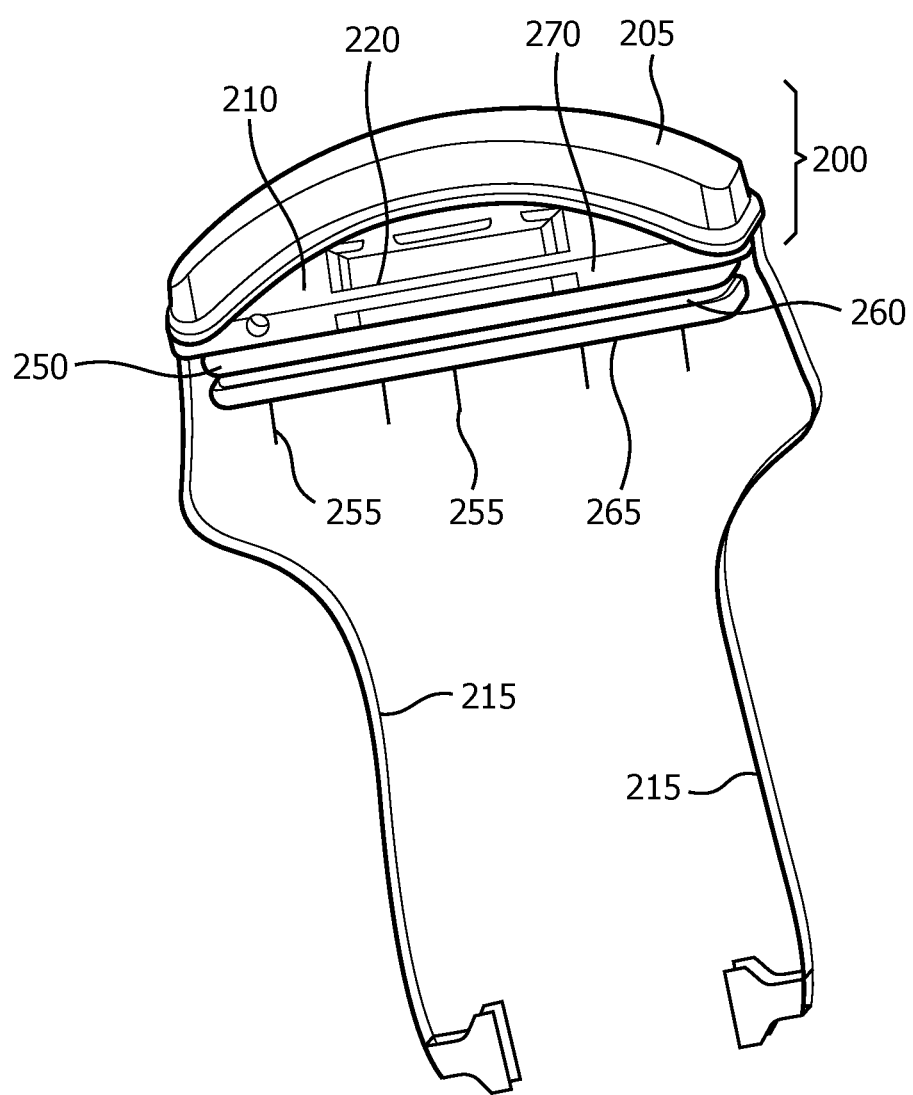
FIG. 2 is a schematic illustration of a transducer assembly and heat sink according to an embodiment of the disclosure.

FIG. 2 is a schematic illustration of a transducer assembly 200 and heat sink 250 according to an embodiment of the disclosure. The transducer assembly 200 and/or heat sink 250 may be used in combination with a fluid chamber, such as fluid chamber 100 illustrated in FIG. 1. The transducer assembly 200 may include a lens 205, a transducer stack 210, and one or more flexible circuits 215. The lens 205 may be coupled to an upper surface of the transducer stack 210. The lens 205 may acoustically couple the transducer stack 210 to an object to be imaged. The transducer stack 210 may include one or more ultrasound transducer elements. The transducer stack 210 may include supporting electronic components for the transducer elements. For example, electrical coupling to a power supply, control signals, data signals, and/or other circuits. The flexible circuits 215 may be coupled to a lower surface and/or edge of the transducer stack 210. The flexible circuits 215 may electrically couple transducer elements and/or other electronic components of the transducer stack 210 to additional electronic components in an ultrasound probe or components of an ultrasound imaging system (not shown). The flexible circuits 215 may provide electrical power and/or communication between the transducer stack 210 and other components.

The heat sink 250 may be a rectangular plate having an upper surface 270 and a lower surface 265 parallel to the upper surface 270. The upper surface 270 of a heat sink 250 may be positioned against the lower surface 220 of the transducer assembly 200. In some embodiments, the lower surface 220 may be a lower surface of an acoustic backing included in the transducer assembly 200. The heat sink 250 may be coupled to the transducer assembly 200 by fasteners (e.g., screws), adhesives (e.g., epoxy), and/or compression. In some embodiments, a thermally conductive laminate may be applied to the upper surface 270 of the heat sink and/or the lower surface 220 of the transducer assembly 200 to increase heat transfer from the transducer assembly 200 to the heat sink 250. The upper surface 270 of the heat sink 250 may be contoured to be flush against the lower surface 220 of the transducer assembly 200. The upper surface 270 of the heat sink 250 may be sized to cover the lower surface 220 of the transducer assembly. In some embodiments, the upper surface 270 of the heat sink 250 may be sized to cover a portion of the lower surface 220 of the transducer assembly.

The heat sink 250 may be implemented with aluminum, another metal, and/or another heat conducting material.

In some embodiments, the heat sink 250 includes a gland 260 extending around a periphery of the heat sink 250. The gland 260 may be configured to accept an O-ring (not shown). The O-ring may facilitate the formation of a fluid-impermeable coupling between the heat sink 250 and a fluid chamber (not shown), such as fluid chamber 100 illustrated in FIG. 1. The O-ring may engage an inner surface of an outer shell of the fluid chamber and/or an upper rim of the outer shell. In some embodiments, the O-ring and gland 260 may be omitted. For example, if an upper surface of the outer shell is closed, the heat sink 250 may be coupled to the outer shell by compression, a thermal laminate, and/or other coupling method. In some embodiments, if the upper surface of the outer shell is closed, the heat sink 250 may be omitted, and the transducer assembly 200 may be coupled to the upper surface of the fluid chamber.

In some embodiments, a lower surface 265 of the heat sink 250 may include one or more fins 255 extending from the lower surface 265. The fins 255 may extend perpendicularly from the lower surface or at another angle. The fins 255 may be parallel to one another or intersect. The fins 255 may form straight lines or another pattern (e.g., waves, concentric circles, zig-zags). In some embodiments, the pattern formed by the fins 255 may be chosen to induce a desired circulation pattern of a fluid in contact with the fins 255. The fins 255 may be in contact with an upper surface of a fluid chamber. If the upper surface of the fluid chamber is open, the fins 255 may extend into the interior of the fluid chamber. The fins 255 may contact a coolant within the fluid chamber. In some embodiments, the fins 255 are omitted, and the lower surface 265 of the heat sink 250 is flat or contoured to be flush against the upper surface of the fluid chamber.

Figure 3:
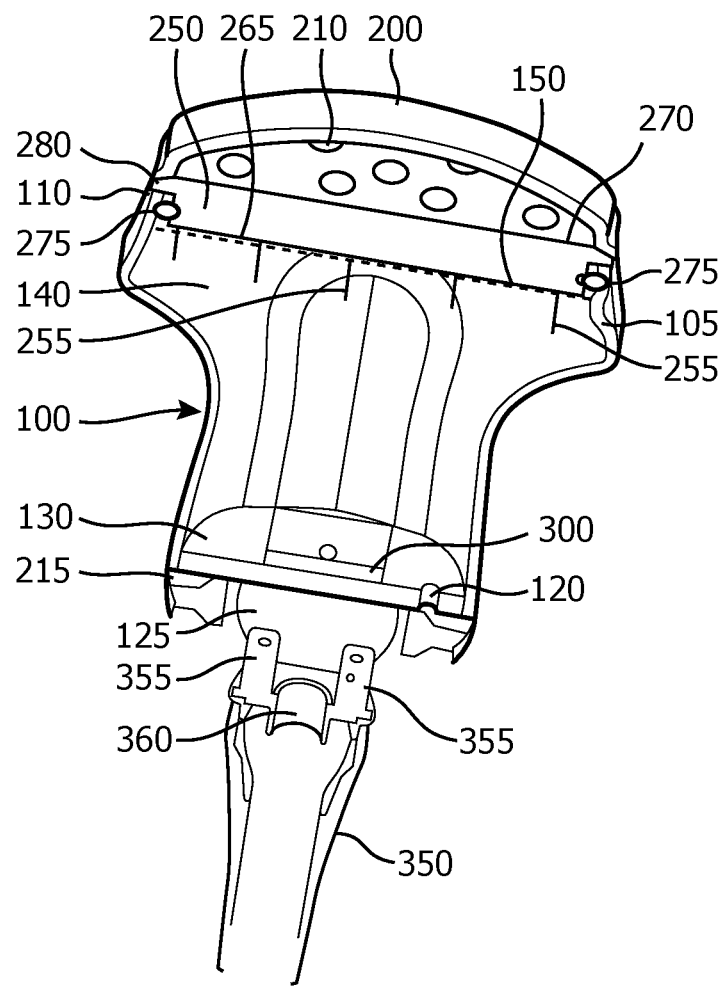
FIG. 3 is a schematic illustration of a cross sectional view of a fluid chamber, heat sink, and transducer assembly according to an embodiment of the disclosure.

FIG. 3 is a schematic illustration of a cross sectional view of a fluid chamber 100, heat sink 250, and transducer assembly 200 according to an embodiment of the disclosure. The transducer assembly 200 may be in contact with the heat sink 250. The transducer assembly 200 may also be in contact with the fluid chamber 100 in some embodiments. The heat sink 250 may be in contact with the fluid chamber 100. The flexible circuits 215 of the transducer assembly 200 may extend on either side of the heat sink 250 and extend on either side of the fluid chamber 100. The flexible circuits 215 may extend through grooves (not shown) of the outer shell 105 of the fluid chamber 100. For example, the flexible circuits 215 may extend through grooves 115 illustrated in FIG. 1. In some embodiments, the flexible circuits 215 extend beyond the fluid chamber 100 as shown in FIG. 3. The flexible circuits 215 may couple to one or more PCB's (not shown), a cable assembly 350, and/or other ultrasound probe component.

As shown in FIG. 3, in some embodiments, the heat sink 250 may be at least partially enclosed by the fluid chamber 100. The heat sink 250 may be press fit into the fluid chamber 100. An O-ring 275 around a periphery of the heat sink 250 may engage an inner surface 140 of the fluid chamber 100 to form a fluid-impermeable seal. The O-ring 275 may be positioned within a gland (not shown), such as gland 260 illustrated in FIG. 2. The O-ring 275 may be implemented with rubber, silicone, and/or other fluid-impermeable, resilient material.

In some embodiments, the heat sink 250 may include a flange 280 that extends around and beyond a periphery of the heat sink 250 proximate the upper surface 270. The flange 280 may be between the O-ring 275 and the upper surface 270. The flange 280 may contact an upper surface and/or rim 110 of the fluid chamber 100. The flange 280 may act as a stop to prevent the heat sink 250 from being fully enclosed by the fluid chamber 100. The engagement of the flange 280 and upper surface and/or rim 110 of the fluid chamber 100 may enhance the fluid-impermeable seal formed by the O-ring 275 and the inner surface 140. In some embodiments, the flange 280 may extend from the heat sink 250 to be flush with the outer surface of the outer shell 105. In some embodiments, the flange 280 may extend beyond the outer shell 105. In some embodiments, the flange 280 may be omitted. For example, the O-ring 275 may act as a stop to prevent the heat sink 250 from being fully enclosed by the fluid chamber 100. In another example, the sides of the heat sink 250 may be tapered so that the lower surface 265 has a smaller area than the upper surface 270. The area of the upper surface 270 may be greater than an area of an opening of the fluid chamber 100.

The lower surface 265 of the heat sink 250 may be in contact with a coolant 150 in the fluid chamber 100. The coolant 150 may dissipate heat from the lower surface 265. As described previously in reference to FIG. 2, the lower surface 265 may include fins 255 that extend into the coolant 150. The fins 255 may increase the surface area of the heat sink 250 in contact with the coolant 150. This may increase heat transfer between the heat sink 250 and the coolant. In some embodiments, the fins 255 may be omitted, and the lower surface 265 may be in contact with and/or submerged in the coolant.

The coolant 150 may be a non-electrically conductive coolant, for example mineral oil or silicone oil. In some embodiments, the coolant 150 is an electrically conductive coolant, for example, water or propylene glycol. In some embodiments, the coolant 150 is a gas such as air, nitrogen, or helium. Other coolants may be used. A mixture of coolants may be used.

The coolant 150 may fully fill the fluid chamber 100. This may facilitate heat dissipation throughout the fluid chamber 100. In some embodiments, the coolant 150 may not fully fill the fluid chamber 100. The coolant 150 may dissipate heat throughout the fluid chamber 100, even when it does not fully fill the fluid chamber 100. The coolant 150 may or may not expand and/or contract over the temperature range of the ultrasound probe. If the coolant 150 expands and/or contracts over the temperature range, a compliant compensation bladder (not shown) may be included in the fluid chamber 100. In some embodiments, the compensation bladder may be coupled to a sealed port, which may be similar to sealed port 120, which may allow contraction and expansion of the compensation bladder. The compensation bladder may be implemented using rubber, a polymer, and/or another coolant-impermeable elastic material.

The coolant 150 may be circulated to increase heat dissipation from the heat sink 250 to the coolant 150. The coolant 150 may be circulated by manual agitation of the fluid chamber 100. For example, a sonographer may agitate the fluid chamber 100 to provide sufficient coolant circulation by moving an ultrasound probe including the fluid chamber 100 during an exam. In some embodiments, the fluid chamber 100 may include a circulation device 300. As shown in FIG. 3, the circulation device 300 may be coupled to the bottom surface 130 of the fluid chamber 100 in some embodiments. However, the circulation device 300 may be coupled to another portion of the inner surface 140 of the fluid chamber 100. Electrical coupling may be provided to the circulation device by sealed port 120. In some embodiments, the circulation device 300 may be a piezoelectric pump that circulates the coolant within the fluid chamber. In some embodiments, the piezoelectric pump may be parylene coated. Other pump types may also be used. In some embodiments, the circulation device 300 may be an impeller. In some embodiments, the circulation device 300 may be a fan. The circulation device 300 may circulate the coolant 150 within the fluid chamber 100 during operation of the ultrasound probe. In some embodiments, the circulation device 300 may continue to circulate the coolant 150 for a period of time after the ultrasound transducer has been used to dissipate remaining heat from the heat sink 250 and/or transducer assembly 200.

In some embodiments, the operation of the circulation device 300 may be based, at least in part, on signals received from one or more sensors (not shown). For example, a temperature sensor may be included with the fluid chamber 100, transducer assembly 200, and/or heat sink 250. The circulation device 300 and/or a circulation device controller (not shown) may be programmed to increase circulation of the coolant 150 when the temperature sensor detects a temperature above a threshold temperature. In another example, an accelerometer may be included in the ultrasound probe. The circulation device 300 and/or a circulation device controller may be programmed to circulate the coolant 150 when the accelerometer detects the ultrasound probe is not being moved by the sonographer to adequately agitate the coolant 150.

Still referring to FIG. 3, tabs 355 may couple to tang 125 to couple the fluid chamber 100 to a bend relief ferrule 360 of a cable assembly 350. The tabs 355 may be coupled to the tang 125 using a fastener (e.g. screw), soldering, and/or other coupling method. The tabs 355 and relief ferrule 360 may be implemented using metal and/or plastic. In some embodiments, the tabs 355 and relief ferrule 360 may dissipate heat from the tang 125 to the cable assembly 350. The cable assembly 350 may provide power to the fluid chamber 100, flexible circuits 215, and/or other ultrasound probe components. The cable assembly 350 may also receive and transmit data and/or control signals to the fluid chamber 100, flexible circuits 215, and/or other ultrasound probe components. The cable assembly 350 may couple the ultrasound probe components to an ultrasound imaging system (not shown).

In an alternative embodiment, the lower surface 265 of the heat sink 250 may be in contact with the upper surface 110 of the fluid chamber 100 (not shown in FIG. 3). The O-ring 275, gland 265, and flange 280 of the heat sink 250 may be omitted. The lower surface 265 may be flush with the upper surface 110. In some embodiments, a thermal laminate may be applied to the lower surface 265 and/or upper surface 110 to reduce thermal resistance. Heat may be dissipated from the transducer assembly 200 through the heat sink 250 to the upper surface 110. The coolant 150 may dissipate heat from the upper surface 110 throughout the fluid chamber 100. The closed fluid chamber 100 may provide resistance to leakage of coolant 150 in the ultrasound probe.

Figure 4:
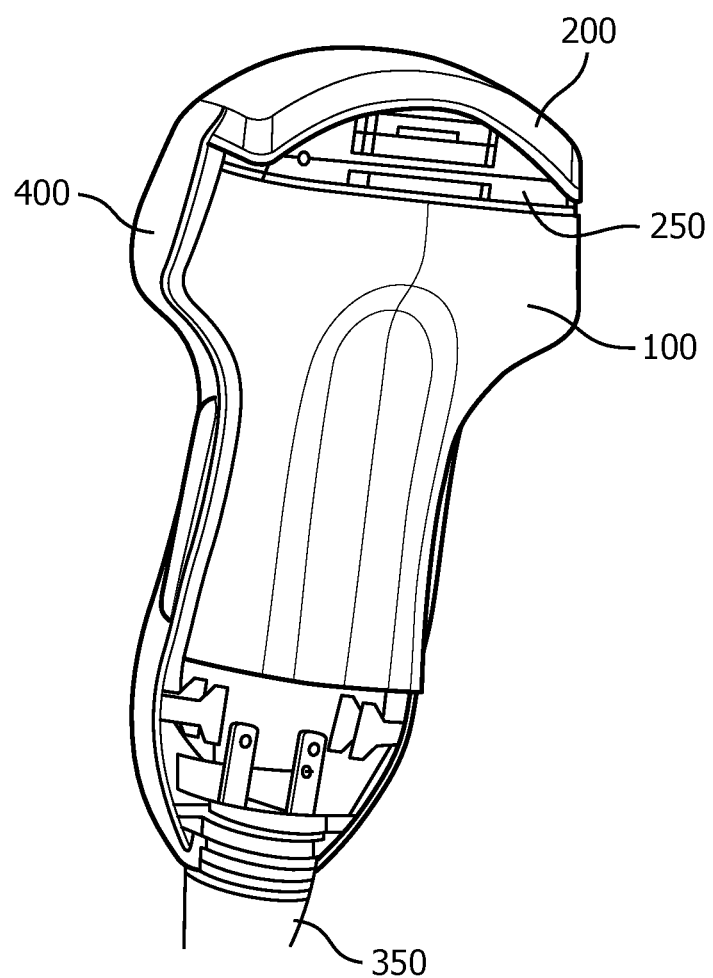
FIG. 4 is a schematic illustration of a side view of a fluid chamber, heat sink, transducer assembly, cable assembly, and a portion of a probe housing according to an embodiment of the disclosure.

FIG. 4 is a schematic illustration of a side view of a fluid chamber 100, heat sink 250, transducer assembly 200, cable assembly 350, and a portion of a probe housing 400 according to an embodiment of the disclosure. The probe housing 400 may enclose the fluid chamber 100, heat sink 250, at least a portion of the transducer assembly 200, and at least a portion of the cable assembly 350. The probe housing 400 may conform to the outer surface of the fluid chamber 100. In some embodiments, the probe housing 400 may dissipate heat from the outer surface of the fluid chamber 100 to the air surrounding an ultrasound probe. In some embodiments, the probe housing 400 may include a heat spreader (not shown) on an inner surface of the probe housing that is in contact with the outer surface of the fluid chamber 100. The heat spreader may reduce thermal resistance between the probe housing 400 and the fluid chamber 100. In some embodiments, the heat spreader may include a thermal interface material between the heat spreader and the fluid chamber 100.

Figure 5:
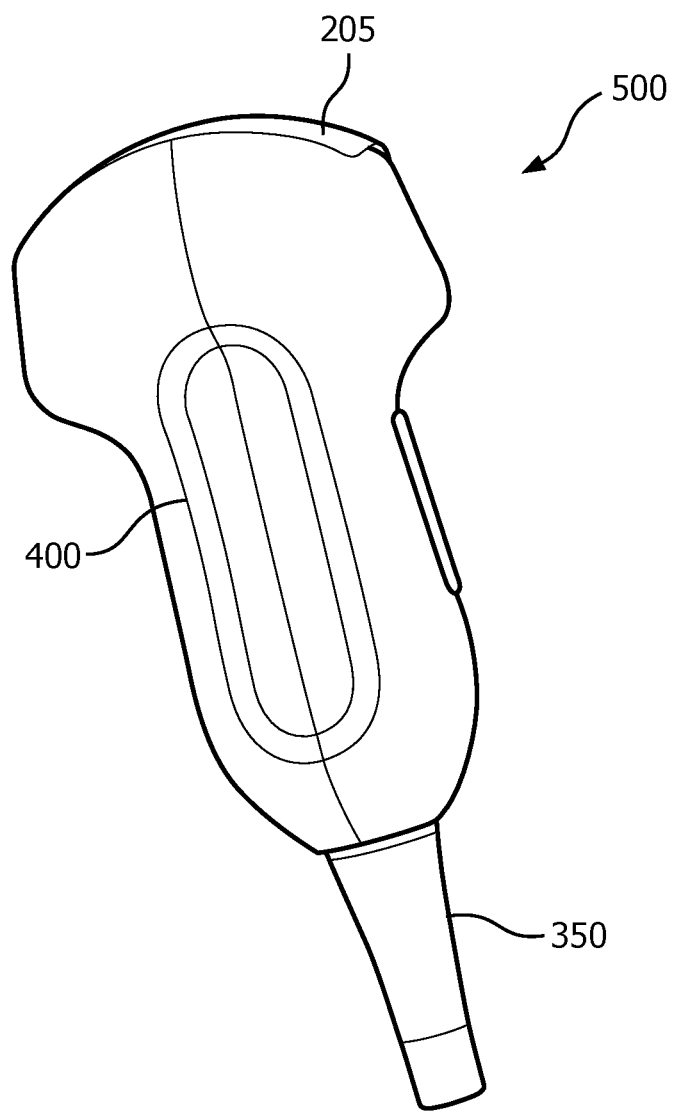
FIG. 5 is a schematic illustration of an ultrasound probe according to an embodiment of the disclosure.

FIG. 5 is a schematic illustration of an ultrasound probe 500 according to an embodiment of the disclosure. The probe housing 400 may enclose all of the components of the probe except for the lens 205 and a portion of the cable assembly 350. In some embodiments, the probe housing 400 is a thermoplastic shell. In some embodiments, the probe housing 400 is omitted, and a robust finish is applied to the exterior of the fluid chamber 100 which may act as a handle for the probe.

Figure 6:
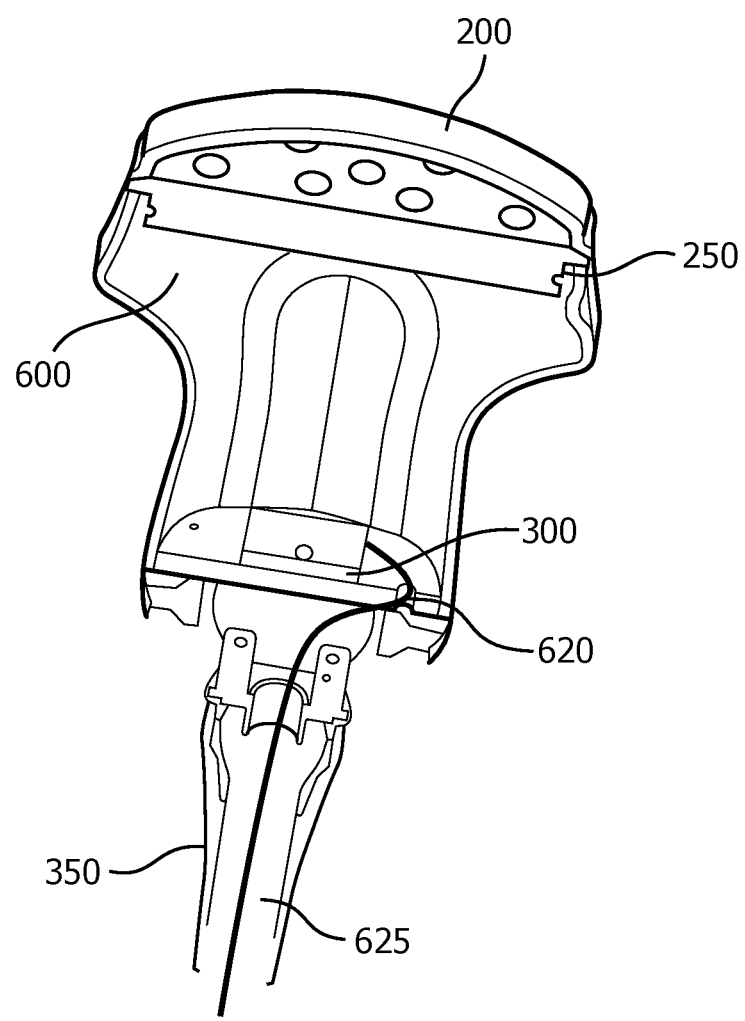
FIG. 6 is a schematic illustration of a cross sectional view of an alternative fluid chamber, heat sink, and transducer assembly according to an embodiment of the disclosure.

FIG. 6 is a schematic illustration of a cross sectional view of an alternative fluid chamber 600, heat sink 250, and transducer assembly 200 according to an embodiment of the disclosure. In the embodiment illustrated in FIG. 6, the coolant is a gas, for example, air. The circulation device 300 may be a fan, an air pump, and/or another suitable gas circulator. The circulation device 300 may be included in a zero insertion force (ZIF) enclosure in some embodiments. Other connector types may also be used. Power may be provided via the cable assembly 350 via port 620. Gas may also pass through port 620 into the fluid chamber 600. The gas may be circulated by the circulation device 300 to dissipate heat from the heat sink 250. The heat sink 250 may be configured similarly to the heat sinks previously described with reference to FIGS. 2-4. In some embodiments, the fluid chamber 600 may include multiple ports to allow passage of gas into and out of the fluid chamber 600. In some embodiments, the ports may include a mesh, filter, and/or barrier material to prevent moisture and/or debris from passing through the ports. In some embodiments, the fluid chamber 600 may be omitted and gas may circulate within a probe housing.

In some embodiments, gas may be provided to the circulation device 300 by a tube 625. The tube 625 may be coupled to the circulation device 300 and pass through the port 620 and into the cable assembly 350. The distal end (not shown) of the tube 625 may be coupled to an air supply. The gas supply may be filtered to reduce introducing dust and/or other contaminants into the ultrasound probe. The gas supply may be chilled which may increase heat dissipation from the heat sink 250. After circulation by the circulation device 300, the gas may be exhausted via port 620 and/or additional ports in the fluid chamber 600. The gas may exit the ultrasound probe via interstitial areas of the cable assembly. In some embodiments, gas may be exhausted via a separate exhaust tube (not shown). The separate exhaust tube may pass through port 620 or a separate port. The distal end of the exhaust tube may be coupled to the gas supply.

In some embodiments, pressurized gas may be provided to the fluid chamber 600 by tube 625. The circulation device 300 may be omitted when pressurized gas is utilized. The pressure of the gas may provide for circulation of the gas within the fluid chamber 600.

Figure 7:
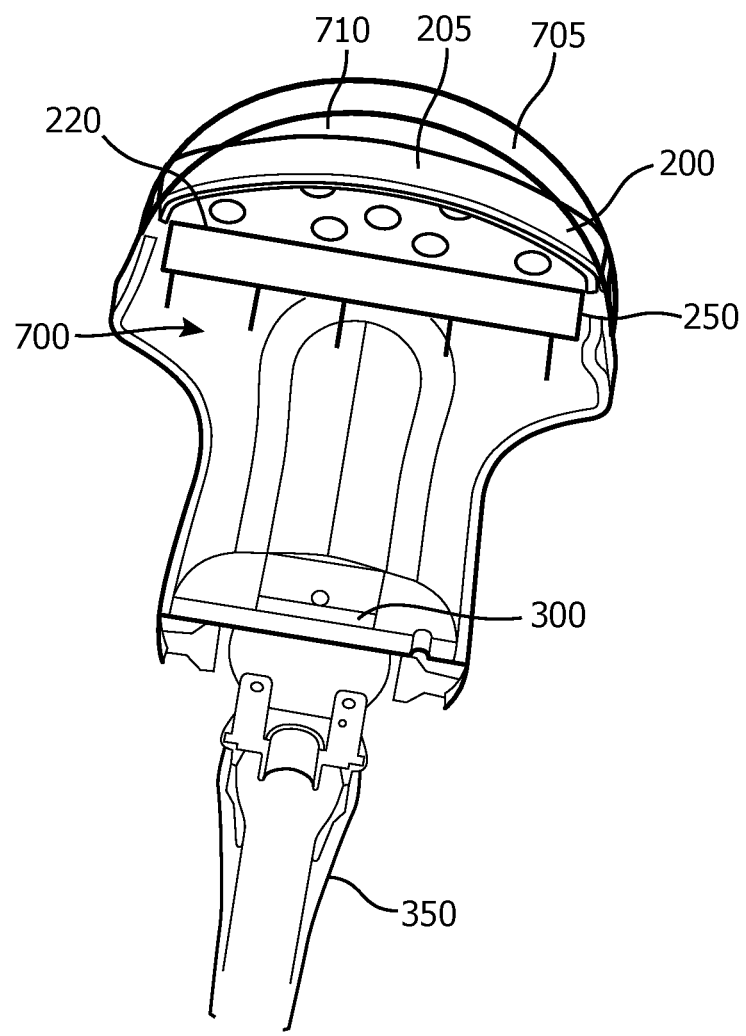
FIG. 7 is a schematic illustration of a cross sectional view of an alternative fluid chamber, heat sink, and transducer assembly according to an embodiment of the disclosure.

FIG. 7 is a schematic illustration of a cross sectional view of an alternative fluid chamber 700, heat sink 250, and transducer assembly 200 according to an embodiment of the disclosure. The fluid chamber 700 may extend to enclose a portion of the transducer assembly 200. A window 705 may be coupled to the fluid chamber 700 and/or probe housing (not shown) and offset over the lens 205 to form an enclosure 710. The window 705 may be contoured to match a contour of lens 205. The window 705 may be contoured to provide an enclosure 710 of a desired shape and/or volume, for example, a dome. The window 705 may be plastic and/or other fluid-impermeable material that provides acoustical coupling to a subject. The window 705 may be acoustically transparent. The enclosure 710 may be fluidly coupled to the fluid chamber 700. Coolant may fill the fluid chamber 700 and the enclosure 710. The coolant may dissipate heat from the lens 205. The coolant may provide acoustical coupling between the window 705 and the lens 205. In some embodiments, the heat sink 250 may be omitted, and the coolant may dissipate heat from the lower surface 220 of the transducer assembly 200.

Although the present system has been described with reference to an ultrasound imaging system, the present system may be extended to other ultrasound transducers. Additionally, the present system may be used to obtain and/or record image information related to, but not limited to renal, testicular, prostate, breast, ovarian, uterine, thyroid, hepatic, lung, musculoskeletal, splenic, nervous, cardiac, arterial and vascular systems, as well as other imaging applications related to ultrasound-guided interventions and other interventions which may be guided by real-time medical imaging. Further, the present system may also include one or more elements which may be used with non-ultrasound imaging systems with or without real-time imaging components so that they may provide features and advantages of the present system.

Further, the present methods, systems, and apparatuses may be applied to existing imaging systems such as, for example, ultrasonic imaging systems. Suitable ultrasonic imaging systems may include a Philips® ultrasound system which may, for example, support a conventional broadband linear array transducer that may be suitable for small-parts imaging.

Certain additional advantages and features of this invention may be apparent to those skilled in the art upon studying the disclosure, or may be experienced by persons employing the novel system and method of the present invention, chief of which is thermal dissipation in ultrasound transducers and method of operation thereof is provided. Another advantage of the present systems and method is that conventional medical image systems may be easily upgraded to incorporate the features and advantages of the present systems, devices, and methods.

Of course, it is to be appreciated that any one of the above embodiments or processes may be combined with one or more other embodiments and/or processes or be separated and/or performed amongst separate devices or device portions in accordance with the present systems, devices and methods.

Finally, the above-discussion is intended to be merely illustrative of the present system and should not be construed as limiting the appended claims to any particular embodiment or group of embodiments. Thus, while the present system has been described in particular detail with reference to exemplary embodiments, it should also be appreciated that numerous modifications and alternative embodiments may be devised by those having ordinary skill in the art without departing from the broader and intended spirit and scope of the present system as set forth in the claims that follow. Accordingly, the specification and drawings are to be regarded in an illustrative manner and are not intended to limit the scope of the appended claims.

What is claimed is:

1. An ultrasound probe comprising:
   a hand-held probe housing;

a transducer assembly including a transducer, wherein at least a portion of the transducer assembly is enclosed by the hand-held probe housing; and a fluid chamber coupled to the transducer assembly and configured to dissipate heat from the transducer assembly, wherein the fluid chamber is completely enclosed by the hand-held probe housing, the fluid chamber comprising:

an outer shell having an upper surface and a bottom surface, wherein the upper surface is proximate to the transducer assembly and the bottom surface is spaced from the transducer assembly;

an interior defined by the outer shell and configured to contain a liquid coolant, wherein the fluid chamber is configured to receive and seal the liquid coolant within the interior, wherein the interior is hollow such that the interior does not have a conduit associated with the liquid coolant; and a circulation device disposed within the conduit-free interior, wherein the circulation device is configured to circulate the liquid coolant only within the interior.

2. The ultrasound probe of claim 1, further comprising a heat sink configured to dissipate heat from the transducer assembly to the fluid chamber, the heat sink comprising:

a surface coupled to a first surface of the transducer assembly;

an additional surface in contact with the fluid chamber;

a gland around a periphery of the heat sink; and an O-ring disposed in the gland.

3. The ultrasound probe of claim 2, wherein the O-ring is configured to engage the interior to form a fluid-impermeable seal.

4. The ultrasound probe of claim 2, wherein the additional surface includes a fin extending from the additional surface into the interior.

5. The ultrasound probe of claim 2, wherein the heat sink further includes a flange around the periphery proximate the surface coupled to the first surface of the transducer assembly, the flange configured to contact a rim of the upper surface of the outer shell.

6. The ultrasound probe of claim 1, further comprising:

a sealed port through the outer shell, wherein the sealed port is configured to allow electrical coupling of a power source to the circulation device.

7. The ultrasound probe of claim 1, wherein the fluid chamber further comprises a tang extending from the bottom surface of the outer shell, wherein the tang is configured to couple the fluid chamber to a cable assembly.

8. The ultrasound probe of claim 1, wherein the fluid chamber includes grooves in the outer shell configured to accept a flexible circuit coupled to the transducer assembly, wherein the grooves are positioned such that the flexible circuit is disposed between the hand-held probe housing and the outer shell within the hand-held probe housing.

9. The ultrasound probe of claim 1, further comprising an accelerometer disposed within the hand-held probe housing, wherein the circulation device is configured to circulate the liquid coolant based on movement of the ultrasound probe not being detected by the accelerometer.

10. The ultrasound probe of claim 1, further comprising an enclosure formed over a lens of the transducer assembly, wherein the enclosure is fluidly coupled to the fluid chamber such that the interior comprises the enclosure.

11. An active thermal management system for an ultrasound probe, the active thermal management system comprising:

a hand-held probe housing; and a fluid chamber configured to couple to a transducer assembly of the ultrasound probe and configured to dissipate heat from the transducer assembly, wherein the fluid chamber is completely enclosed by the hand-held probe housing, the fluid chamber comprising:

an outer shell having an upper surface and a bottom surface, wherein the upper surface is proximate to the transducer assembly and the bottom surface is spaced from the transducer assembly;

an interior defined by the outer shell and configured to contain a liquid coolant, wherein the interior is hollow such that the interior does not have a conduit associated with the liquid coolant;

a circulation device located within the conduit-free interior and configured to circulate the liquid coolant within the interior; and a sealed port through the outer shell, wherein the sealed port is configured to allow electrical coupling of a power source to the circulation device and wherein the sealed port is further configured to seal the liquid coolant within the interior.

12. The active thermal management system of claim 11, wherein the circulation device comprises a pump or an impeller.

13. The active thermal management system of claim 11, further comprising a temperature sensor coupled to the fluid chamber and configured to detect a temperature of the fluid chamber.

14. The active thermal management system of claim 13, further comprising a controller configured to increase circulation of the liquid coolant by the circulation device when the temperature sensor detects that the temperature of the fluid chamber exceeds a threshold temperature.

15. The active thermal management system of claim 11, wherein the liquid coolant comprises a mixture of gas and liquid.

16. The active thermal management system of claim 11, wherein the circulation device comprises a fan.

* * * * *